United States Patent
Branson et al.

(10) Patent No.: US 10,603,446 B2
(45) Date of Patent: Mar. 31, 2020

(54) IV CATHETER WITH INTEGRAL EXTENSION SET AND A SPRING POWERED NEEDLE SAFETY

(71) Applicant: Becton, Dickinson and Company, Franklin Lakes, NJ (US)

(72) Inventors: Stephanie J Branson, Sandy, UT (US); Weston F Harding, Lehi, UT (US); S Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 278 days.

(21) Appl. No.: 15/477,256

(22) Filed: Apr. 3, 2017

(65) Prior Publication Data
US 2018/0280626 A1 Oct. 4, 2018

(51) Int. Cl.
*A61M 5/32* (2006.01)
*A61M 25/06* (2006.01)
*A61M 25/00* (2006.01)
*A61M 39/10* (2006.01)

(52) U.S. Cl.
CPC ........ *A61M 5/3221* (2013.01); *A61M 5/3232* (2013.01); *A61M 25/0043* (2013.01); *A61M 25/0606* (2013.01); *A61M 25/0631* (2013.01); *A61M 25/0097* (2013.01); *A61M 2039/1072* (2013.01)

(58) Field of Classification Search
None
See application file for complete search history.

(56) References Cited

U.S. PATENT DOCUMENTS

| 4,755,169 | A | * | 7/1988 | Sarnoff | A61M 5/2066 604/136 |
| 5,306,237 | A | * | 4/1994 | Clement | A61B 10/04 604/30 |
| 5,749,857 | A | * | 5/1998 | Cuppy | A61M 25/0606 604/161 |
| 5,749,968 | A | * | 5/1998 | Melanson | A61K 38/42 118/300 |
| 5,755,709 | A | * | 5/1998 | Cuppy | A61M 25/0606 604/164.12 |

(Continued)

FOREIGN PATENT DOCUMENTS

| EP | 0847289 | 4/2004 |
| EP | 1785159 | 5/2007 |

(Continued)

*Primary Examiner* — Bhisma Mehta
*Assistant Examiner* — Matthew A Engel
(74) *Attorney, Agent, or Firm* — Kirton & McConkie; Craig Metcalf; Kevin Stinger

(57) ABSTRACT

Catheter and needle assemblies with spring-powered retractable needles are described. The assemblies can include a hollow handle, a grip portion, a catheter hub with a catheter, and a needle. The needle can have a first position in which the needle is slidably disposed within the catheter and a second position in which the needle is slidably removed from the catheter and retracted at least in part into the hollow handle. The grip portion can include a trigger portion that activates a spring to move the needle from the first position into the second position. In the second position, a sharp distal point of the needle is shielded by the grip portion to prevent accidental needle sticks.

5 Claims, 6 Drawing Sheets

(56) References Cited

U.S. PATENT DOCUMENTS

| | | | | |
|---|---|---|---|---|
| 5,788,677 | A * | 8/1998 | Botich | A61M 5/24 604/110 |
| 5,795,339 | A * | 8/1998 | Erskine | A61M 25/0631 604/171 |
| 6,569,115 | B1 * | 5/2003 | Barker | A61M 5/2429 604/110 |
| 6,949,114 | B2 * | 9/2005 | Milo | A61B 17/0057 604/15 |
| 7,056,306 | B1 * | 6/2006 | Halseth | A61B 5/15003 600/114 |
| 8,262,607 | B2 * | 9/2012 | Porter | A61B 17/00491 604/82 |
| 9,408,983 | B2 * | 8/2016 | Klippenstein | A61M 5/3234 |
| 9,872,971 | B2 * | 1/2018 | Blanchard | A61M 25/0097 |
| 9,950,139 | B2 * | 4/2018 | Blanchard | A61M 25/0105 |
| 10,232,146 | B2 * | 3/2019 | Braithwaite | A61M 25/0631 |
| 2007/0060890 | A1 * | 3/2007 | Cuppy | A61M 25/0631 604/164.01 |
| 2007/0255221 | A1 * | 11/2007 | Nakajima | A61M 25/0017 604/168.01 |
| 2008/0121657 | A1 * | 5/2008 | Voegele | B05C 17/00553 222/137 |
| 2009/0131864 | A1 * | 5/2009 | Pickhard | A61M 5/284 604/83 |
| 2012/0323181 | A1 * | 12/2012 | Shaw | A61M 25/0606 604/164.12 |
| 2016/0008538 | A1 * | 1/2016 | Isaacson | A61M 5/158 604/263 |
| 2016/0067453 | A1 * | 3/2016 | Braithwaite | A61M 25/0631 604/164.08 |
| 2017/0035992 | A1 * | 2/2017 | Harding | A61M 5/34 |
| 2018/0280626 | A1 * | 10/2018 | Branson | A61M 25/0631 |

FOREIGN PATENT DOCUMENTS

| | | |
|---|---|---|
| EP | 2044970 | 4/2009 |
| WO | 00/12160 | 3/2000 |

* cited by examiner

IV CATHETER WITH INTEGRAL EXTENSION SET AND A SPRING POWERED NEEDLE SAFETY

BACKGROUND OF THE INVENTION

This disclosure relates generally to intravenous catheters (e.g., vascular access devices). More specifically, this application discloses various methods for using and systems of catheter and needle assemblies with spring-powered needle safeties. In general, vascular access devices are inserted into veins via peripheral or central vessels for diagnostic or therapeutic reasons. Vascular access devices can be used for infusing fluid (e.g., saline solution, blood, medicaments, and/or total parenteral nutrition) into a patient, withdrawing fluids (e.g., blood) from a patient, and/or monitoring various parameters of the patient's vascular system. Additionally, a convention is followed in this disclosure using the term "proximal" to refer to a portion of a device closest to the medical practitioner and the term "distal" for the portion of the device toward a patient or away from the medical practitioner.

Intravenous (IV) catheter assemblies are among the various types of vascular access devices. Over-the-needle peripheral IV catheters are a common IV catheter configuration. As its name implies, an over-the-needle catheter is mounted over an introducer needle having a sharp distal tip. The introducer needle is generally a venipuncture needle coupled to a needle assembly that helps guide the needle and facilitates its cooperation with the catheter. At least the inner surface of the distal portion of the catheter tightly engages the outer surface of the needle to prevent peelback of the catheter and, thereby, to facilitate insertion of the catheter into the blood vessel. The catheter and the introducer needle are often assembled so that the sharp distal tip of the introducer needle extends beyond the distal tip of the catheter. Moreover, the catheter and needle are often assembled so that during insertion, the bevel of the needle faces up, away from the patient's skin. The catheter and introducer needle are generally inserted at a shallow angle through the patient's skin into a blood vessel.

Following insertion of the catheter and introducer needle into the blood vessel at the catheterization site, the introducer needle is removed leaving the catheter in the blood vessel. The catheter can then be used to infuse fluids into the vasculature of the patient. The removed introducer needle is considered a "blood-contaminated sharp" and must then be properly handled and discarded.

Although conventional over-the-needle catheters may provide a variety of benefits, they are not without their shortcomings. For example, after the introducer needle is removed, it can present a needle stick hazard to the medical practitioner and/or patient. Also, as a blood-contaminated sharp, the removed introducer needle can covered with blood and/or tissue and can present a contamination hazard to the medical practitioner and/or other patients. The needle stick and contamination hazards can be exacerbated in certain situations (e.g., where the catheterized patient is uncooperative or where catheterization takes place in a moving ambulance).

Thus, while a variety of over-the-needle catheters currently exist, challenges still exist, including those listed above. Accordingly it would be an improvement in the art to augment or even replace current systems and techniques with other systems and techniques.

BRIEF SUMMARY OF THE INVENTION

This disclosure relates generally to catheter and needle assemblies with retractable needles. More specifically, this disclosure discusses catheter and needle assemblies with retractable needles that prevent accidental needle sticks. Methods of using these catheter and needle assemblies are also discussed.

Some exemplary catheter and needle assemblies can comprise a hollow handle, a grip portion, a catheter hub comprising a catheter, and an elongate needle having a first position in which the elongate needle is slidably disposed within the catheter and a second position in which the elongate needle is slidably removed from the catheter and retracted at least in part into the hollow handle. In some cases, the catheter hub can further comprise a septum configured to form a fluid-tight seal when the elongate needle is in the second position. In other cases, the grip portion can comprise a trigger portion configured to activate a spring to move the elongate needle from the first position into the second position. In yet other cases, the assembly can include a needle carriage selectively coupled to the elongate needle. In some instances, a spring can drive the needle carriage along elongate cavities within the grip portion and hollow handle to retract the needle from the first position to the second position. In other instances, the needle carriage can comprise a carriage extension configured to detachably couple with a proximal fitting of the catheter hub. In yet other instances, needle carriage can comprise a needle carriage cavity in fluid communication with an open bore of the elongate needle. In some cases, the needle carriage can comprises a neck configured to engage a trigger tab to maintain the elongate needle in the first position. In other cases, the catheter hub comprises a Y-port.

In some embodiments, methods of catheterization comprise providing a catheter and needle assembly comprising a hollow handle, a grip portion, a catheter hub comprising a catheter, and an elongate needle having a first position in which the elongate needle is slidably disposed within the catheter and a second position in which the elongate needle is slidably removed from the catheter and retracted at least in part into the hollow handle, inserting the elongate needle and catheter at a catheter insertion site, activating a trigger portion to activate a spring to move the elongate needle from the first position to the second position, and removing the grip and handle portions containing the retracted elongate needle. In some cases, the catheter hub can further comprise a septum configured to form a fluid-tight seal when the elongate needle is in the second position. In other cases, activating the trigger portion can include depressing a trigger button that disengages a trigger tab that maintains the elongate needle in the first position.

In some embodiments, catheter and needle assemblies comprise a hollow handle coupled to a grip portion, the hollow handle and grip portion comprising an elongate cavity, a catheter hub comprising a catheter, and an elongate needle mounted on a needle carriage, where the needle carriage is slidably disposed within the elongate cavity, and where the elongate needle comprises a first position in which the elongate needle is slidably disposed within the catheter and a second position in which the elongate needle is slidably removed from the catheter and retracted at least in part into the hollow handle. In some cases, the grip portion can comprise a trigger portion configured to activate a spring to slidably drive the needle carriage along the elongate cavity to move the elongate needle from the first position into the second position. In other cases, the catheter hub can further comprise a septum traversed by the elongate needle when the elongate needle is in the first position and configured to form a fluid-tight seal when the elongate needle is slidably removed from the septum as the elongate needle moves to the second position. In yet other cases, the needle carriage can comprise a carriage extension configured to detachably couple with a proximal fitting of the catheter hub when the elongate needle is in the first position. In some instances, the needle carriage can comprise a needle carriage cavity in fluid communication with an open bore of the elongate needle. In other instances, the needle carriage can comprise a neck configured to engage a trigger tab to maintain the elongate needle in the first position. In yet other instances, depressing a trigger button can slide the trigger tab to disengage the neck to retract the elongate needle to the second position. In some cases, a sharp distal point of the elongate needle can be shielded by the grip portion when the elongate needle is in the second position.

BRIEF DESCRIPTION OF THE SEVERAL VIEWS OF THE DRAWINGS

In order that the manner in which the above-recited and other features and advantages of disclosed embodiments are obtained and will be readily understood, a more particular description of the systems and methods briefly described above will be rendered by reference to specific embodiments thereof, which are illustrated in the appended drawings. Understanding that these drawings depict only typical embodiments and are not, therefore, to be considered to be limiting of its scope. Exemplary embodiments of the disclosed systems and methods will be described and explained with additional specificity and detail below through the use of the accompanying drawings in which.

Figure 1:
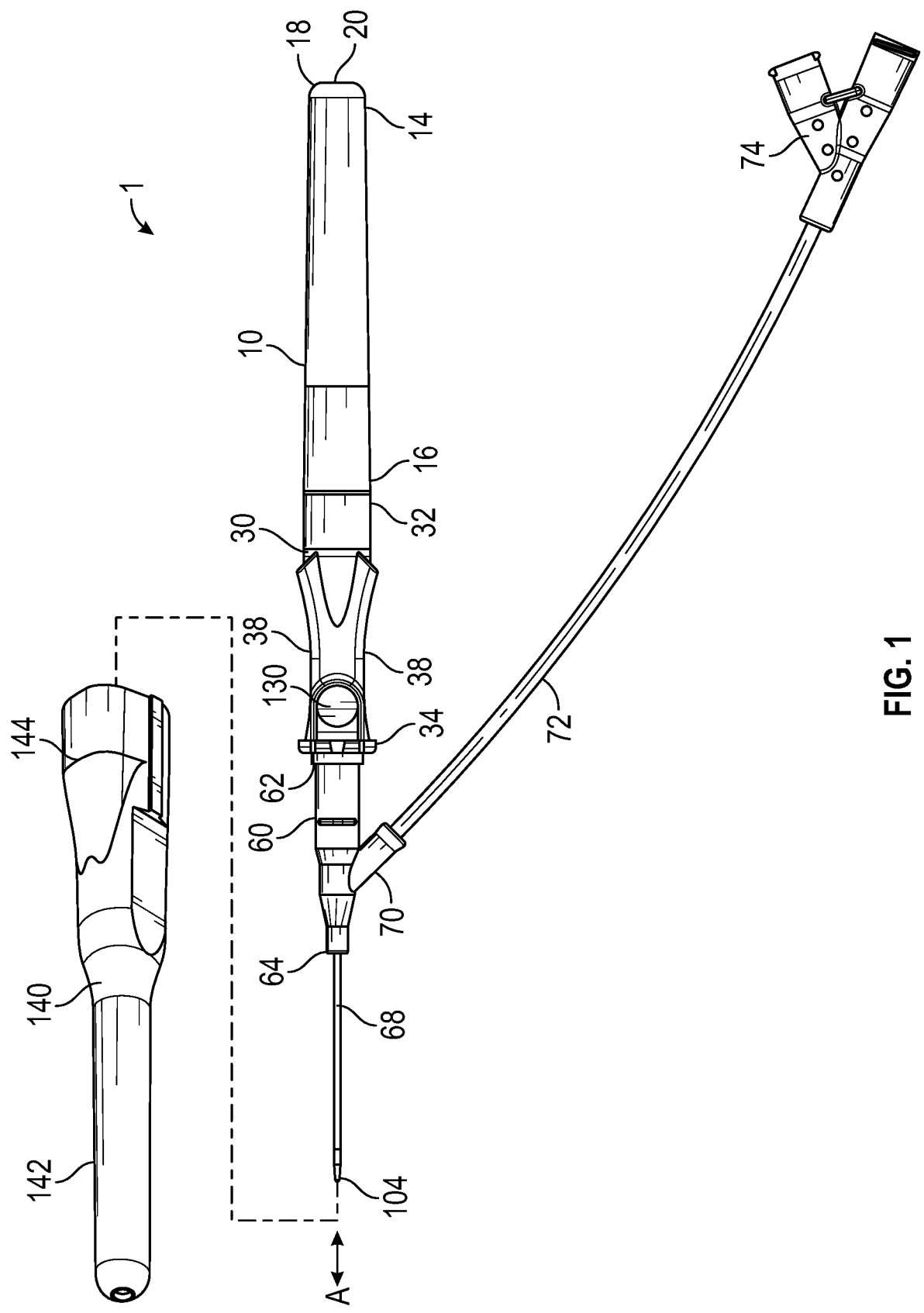
FIG. 1 illustrates a top view of a catheter and needle assembly.

The Figures illustrate specific aspects of exemplary catheter securement dressing and methods for making and using such devices as described below. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices. Moreover, the Figures may show simplified or partial views, and the dimensions of elements in the Figures may be exaggerated or otherwise not in proportion for clarity and instruction.

DETAILED DESCRIPTION OF THE INVENTION

The following description supplies specific details to provide a thorough understanding of the described catheter and needle assemblies. Nevertheless, the skilled artisan would understand that the described catheter and needle assemblies and methods of making and using them can be implemented and used without employing these specific details. Indeed, the catheter and needle assemblies can be placed into practice by modifying the illustrated devices and methods and can be used in conjunction with any other apparatus and techniques conventionally used in the industry.

In general, this disclosure relates to systems of catheter and needle assemblies and methods of catheterization using such catheter and needle assemblies. In some instances, a catheter and needle assembly can comprise a hollow handle, a grip portion, and a catheter hub, arranged in that order along a longitudinal axis. The catheter hub can comprise an over-the-needle-catheter configured for catheterization of a patient. The needle can be configured retract into the grip portion and hollow handle via a spring. Using the grip portion to manipulate the catheter and needle assembly, a medical practitioner can insert the over-the-needle-catheter into a vasculature of the patient at a catheter insertion site. The medical practitioner can then activate a trigger on the grip portion to retract the spring-loaded needle into the grip portion and the hollow handle. The spring-loaded needle retracts into the grip portion and hollow handle to sheath the needle to avoid a needle stick from the retracted needle. The grip portion and hollow handle can then be removed as a single unit from the catheter hub and safely discarded with minimized risk of needle stick and/or contamination.

Figure 2:
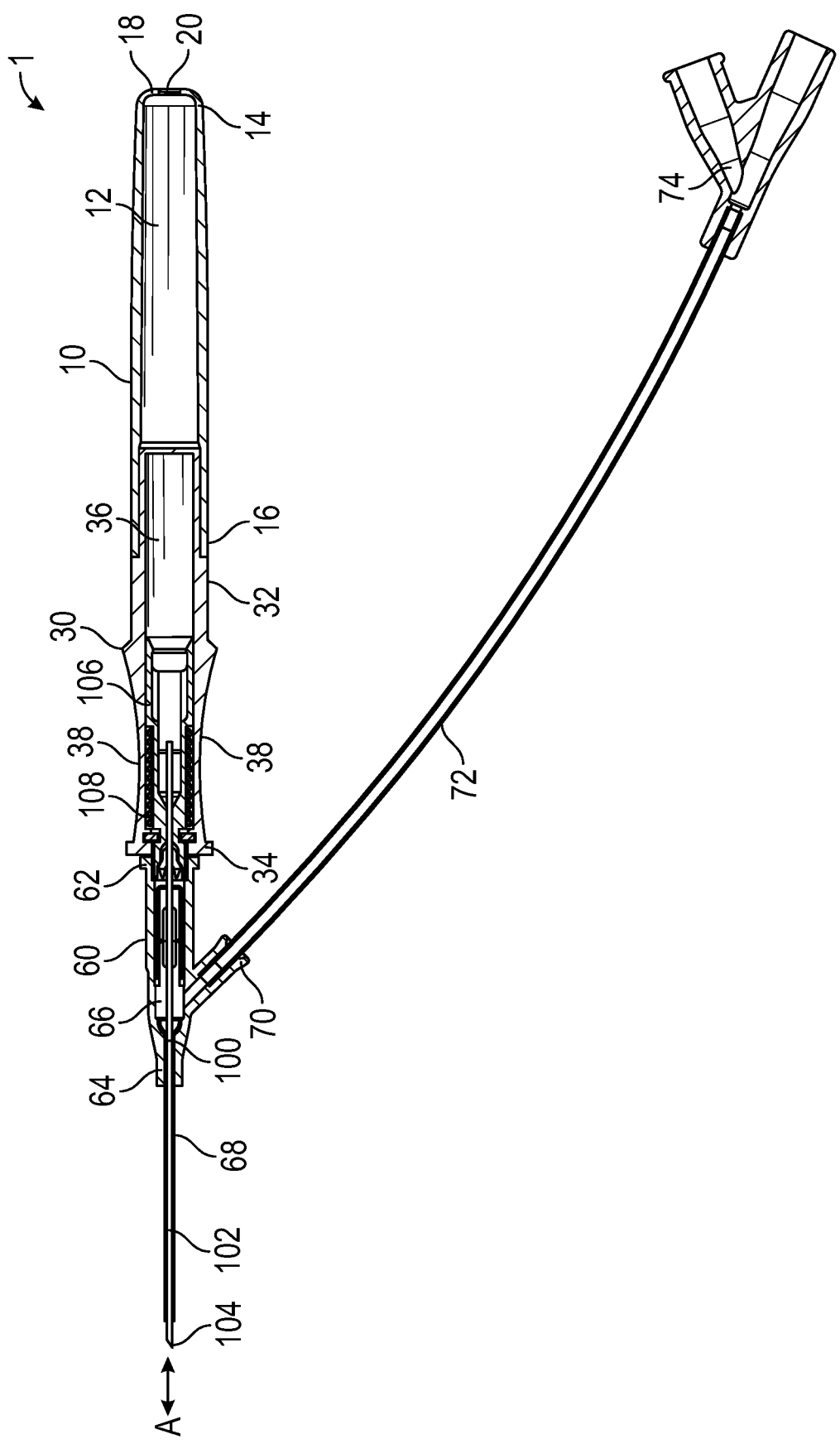
FIG. 2 illustrates a top cutaway view of a catheter and needle assembly.

Referring to FIGS. 1-2, a catheter and needle assembly 1 is shown. While the catheter and needle assembly 1 can comprise any suitable component and/or suitable structure, at least in some embodiments, it comprises a hollow handle 10, a grip portion 30, and a catheter hub 60. In some instances, the hollow handle 10, the grip portion 30, and the catheter hub 60 can be aligned along a longitudinal axis "A". The hollow handle 10 can comprise an elongate cavity 12 aligned along the longitudinal axis "A". The hollow handle 10 can comprise a proximal end 14 and a distal end 16. The proximal end 14 of the hollow handle 10 can comprise an axial opening 18 that includes a vent 20. In some cases, the vent 20 can be configured to selectively allow air transmission into and out of cavity 12 and/or to substantially prevent fluid flow into or out of cavity 12.

In some embodiments, the grip portion 30 comprises a proximal end 32 and a distal end 34. The proximal end 32 of the grip portion 30 can selectively couple with the distal end 16 of the hollow handle 10. The distal end 34 of the grip portion 30 can selectively and detachably couple with a proximal end 62 of the catheter hub 60. The grip portion 30 can also comprise an elongate cavity 36 that extends from the distal end 34 to the proximal end 32 and into the elongate cavity 12 of the hollow handle 10. The grip portion 30 can also comprise gripping surfaces 38 configured to allow the medical practitioner to manipulate the assembly 1 during catheterization. The grip portion 30 can also comprise a trigger portion 130. In some cases, the trigger portion 130 is configured to allow the medical practitioner to retract the spring-loaded needle into the grip portion 30 and hollow handle 10.

In some embodiments, the catheter hub 60 comprises the proximal end 62, a distal end 64, and an open passageway 66 therethrough. In some cases, the proximal end 62 of the catheter hub 60 can be configured to selectively and detachable couple with the distal end 34 of the grip portion 30. In other cases, the catheter hub 60 can comprise a catheter 68 extending distally from the catheter hub 60. In yet other cases the catheter hub 60 can comprise a fluid junction 70 in fluid communication with the catheter 68, tubing 72, and fluid connector 74. In some instances, the tubing 72 can comprise one or more pinch clamps. In other instances, the fluid connector 74 can comprise one or more Luer fittings, a needleless connection, or other means of connecting a fluid line.

In some embodiments, the catheter and needle assembly 1 comprises an elongate needle 100 with an open bore 102 therethrough and a sharp distal point 104. The needle 100 can be slidably disposed within the catheter 68. The needle 100 can be selectively coupled to a needle carriage 106. The needle carriage 106 can be configured to slidably translate within and along the elongate cavity 36 of the grip portion 30 and into the elongate cavity 12 of the handle. The needle 100 can have a first position, best seen in FIGS. 1-3, with needle 100 disposed within the catheter hub 60 within the open passageway 66 and slidably disposed within the catheter 68. In this first position, the needle carriage 106 is disposed within the grip portion 30. The needle 100 can also have a second position, best seen in FIGS. 4A and 4B, with the needle 100 retracted by a helical spring 108 into the grip portion 30 and the hollow handle 10. In this second position, the needle carriage 106 is disposed within the handle 10.

With continued reference to FIGS. 1-2, in some embodiments, the catheter and needle assembly 1 comprises a cover 140. The cover 140 can comprise a distal portion 142 configured to shield the catheter 68 and/or the needle 100. The cover 140 can also comprise a proximal portion 144 configured to shield at least a portion of the catheter hub 60 and the grip portion 30. The proximal portion 144 can also be configured to cover and/or to shield the trigger portion 130 to prevent accidental activation of the trigger portion 130.

Figure 3:
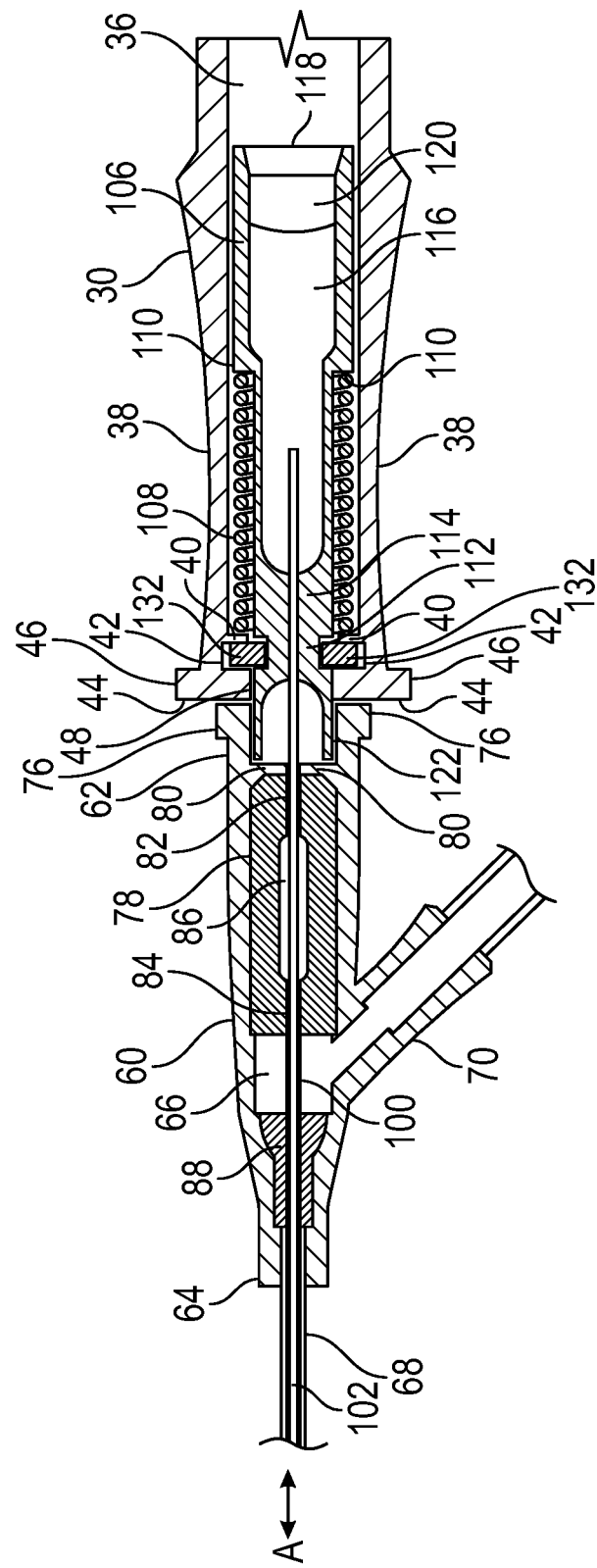
FIG. 3 illustrates a top cutaway view of a catheter hub and grip portion.

Referring now to FIG. 3, a cutaway view of some embodiments of the grip portion 30 and the catheter hub 60 are shown with the needle carriage 106 in the first position. In the first position, the needle carriage 106 can be slidably disposed within the elongate cavity 36 of the grip portion. Also, in this first position, the helical spring 108 can be coiled around a portion of the needle carriage 106 and compressed between a spring tab 110 on the needle carriage 106 and a spring tab 40 on the grip portion 30. The needle carriage 106 can be maintained in this first position with the compressed spring 108 by trigger tabs 132 that slidably engage a neck 112 of the needle carriage 106. The trigger tabs 132 can slidably engage along trigger tab slots 42 in the grip portion 30. The needle 100 can be coupled to the needle carriage 106 by a needle mount 114. The open bore 102 of the needle 100 can open into a needle carriage cavity 116. The needle carriage cavity 116 can open into a needle carriage opening 118. In some cases, the needle carriage opening 118 can further comprise a filter 120.

In some embodiments, the grip portion 30 comprises a distal wall 44. In some cases, the distal wall 44 can comprise wall extensions 46. The distal wall 44 can comprise a distal opening 48. In other cases, the distal wall 44 can be configured to receive a needle carriage extension 122 of the needle carriage 106 such that the needle carriage extension 122 extends at least in part through the distal opening 48 when the needle 100 is in the first position. The needle carriage extension 122 can be configured to extend into and/or be received by a proximal fitting 76 on the catheter hub 60 when the needle 100 is in the first position. The needle carriage extension 122 can also be configured to detachably couple with the proximal fitting 76 on the catheter hub 60 when the needle 100 is in the first position.

In some cases, the proximal fitting 76 can comprise a Luer style fitting. In other cases, the distal wall 44 can be configured to receive the proximal fitting 76. In yet other cases, the needle carriage extension 122 can be configured to extend at least in part into an opening in the proximal fitting 76.

In some embodiments, when the needle 100 is in the first position, the needle 100 extends through the catheter hub 60 through a septum 78 disposed in the open passageway 66 of the catheter hub 60. The septum 78 can be retained within the open passageway 66 by septum retaining tabs 80. The septum 78 can also comprise one or more openings. In some cases, the septum 78 comprises a first septum opening 82 and a second septum opening 84 connected by a septum lumen 86. When in the first position, the needle 100 can also extend through the catheter 68. The catheter 68 can be secured at least in part to the catheter hub 60 with a grommet 88.

Figure 4A:
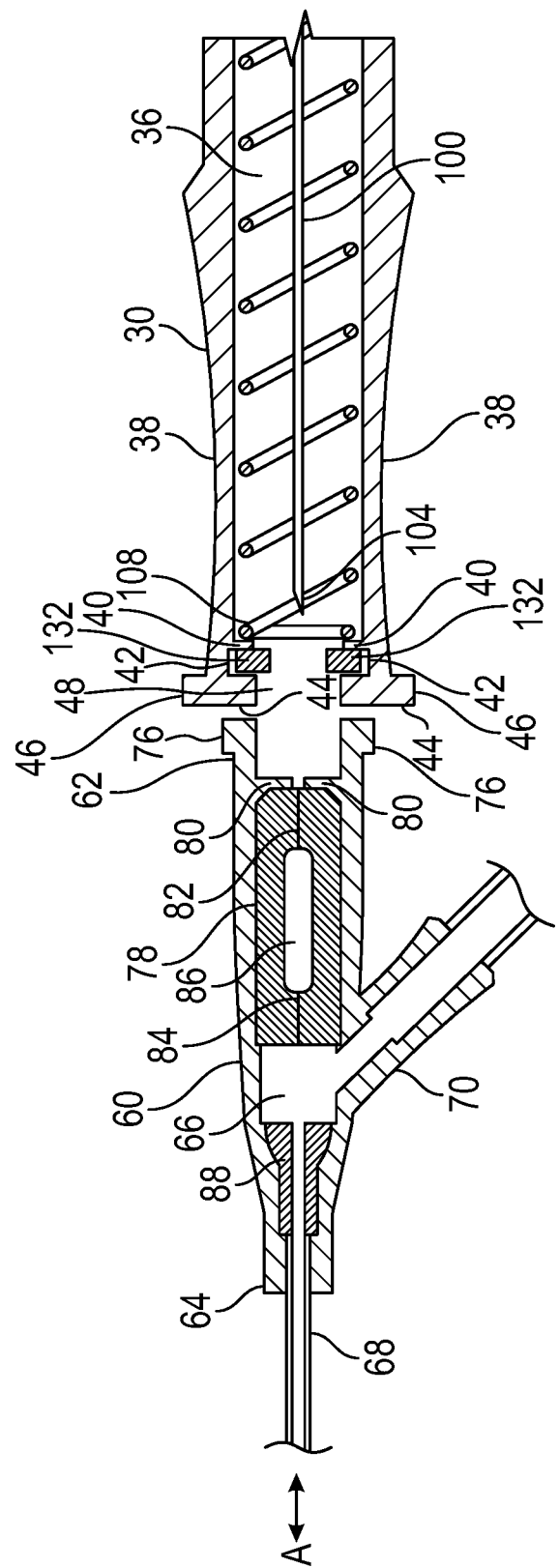
FIG. 4A illustrates a top cutaway view of a catheter hub and grip portion with a needle in a retracted position.
Figure 4B:
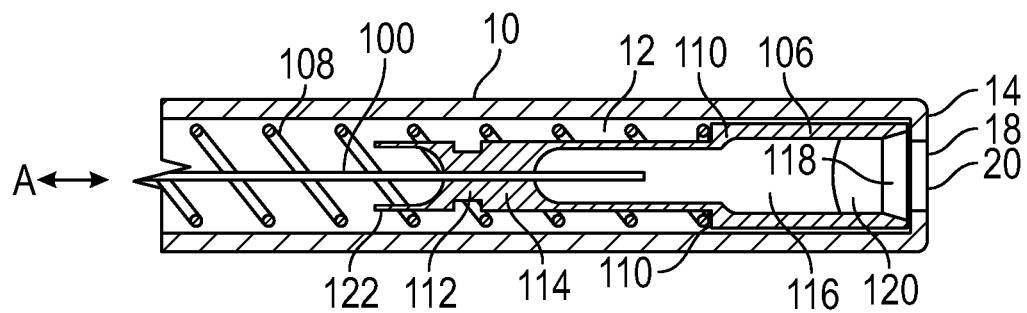
FIG. 4B illustrates a top cutaway view of a hollow handle with a needle in a retracted position.

Referring now to FIGS. 4A and 4B, a cutaway view of some embodiments of the needle and catheter assembly 1 are shown with the needle 100 in the second position. As shown in FIG. 4A, in the second position, the sharp distal point 104 of the needle 100 can be retracted from the catheter hub 60 into the grip portion 30 to prevent accidental needle sticks. In this second position the needle 100 is no longer threaded through the catheter 68. The needle 100 also no longer passes through the septum 78. The needle 100 also no longer passes through the first and second septum openings 82, 84 and the first and second septum openings 82, 84 can maintain a fluid-tight seal. The carriage extension 122 of the needle carriage 106 can also retract from the proximal fitting 76 of the catheter hub 60. In some cases, the catheter hub 60 can separate from the grip portion 30 when the needle 100 is in the second position. In other cases, the catheter hub 60 can remain coupled to the grip portion 30 when the needle 100 is in the second portion and the medical practitioner can separately uncouple the catheter hub 60 from the grip portion 30 after the needle 100 is retracted to the second position.

As shown in FIG. 4B, in the second position, the spring 108 can uncompress and can drive the needle carriage 106 along the elongate cavity 36 of the grip portion 30 and into and along the elongate cavity 12 of the handle 10. Concomitantly, as the needle carriage 106 is driven along the elongate cavities 36, 12, the needle 100 can be slidably withdrawn from the catheter 68 through the septum 78 and into the grip portion 30 and the handle 10. The needle carriage 106 can then come to rest and can be biased against the proximal end 14 of the handle 10. In some instances, the grip portion 30 and handle 10 are then separated from the catheter hub 60 and discarded to prevent any cross-contamination.

Figure 5:
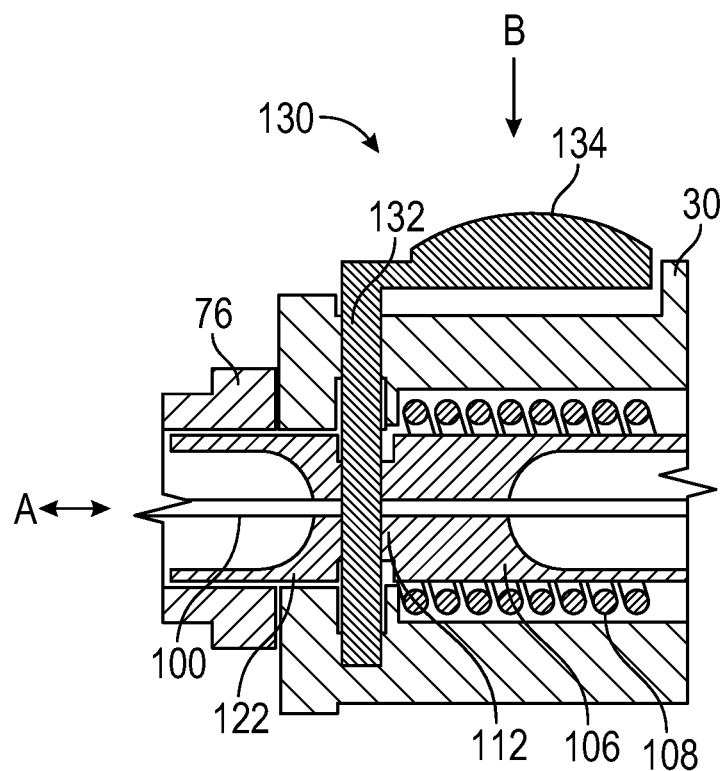
FIG. 5 illustrates a side cutaway view of a trigger portion in relation to a grip portion.
Figure 6A:
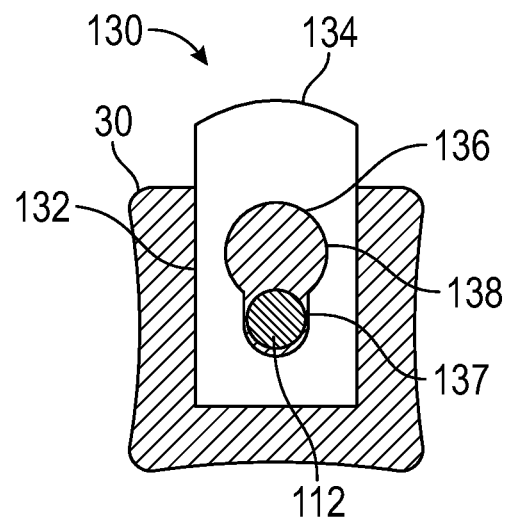
FIG. 6A illustrates a front cutaway view of a trigger portion in an engaged position.
Figure 6B:
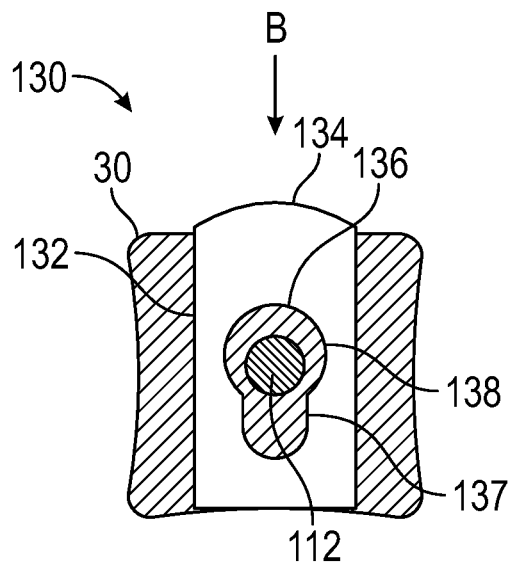
FIG. 6B illustrates a front cutaway view of a trigger portion in a disengaged position.

Referring now to FIGS. 5, 6A, and 6B, some embodiments of the trigger portion 130 are shown. While the trigger portion 130 can comprise any suitable component that allows it to function as intended, at least in some embodiments it comprises the trigger tab 132, a trigger button 134, and a keyhole opening 136 on the trigger tab 132. FIG. 5 shows a side cutaway view of the trigger portion 130 with respect to the grip portion 30. As shown in FIG. 5 and as described above, the trigger tab 132 can be configured to be disposed within the trigger tab slots 42 to engage the neck 112 of the needle carriage 106. When the neck 112 is engaged by the trigger tab 132, the needle 100 is held in the first position. The trigger button 134 can be connected to the trigger tab 132. The trigger button 134 can be configured to allow the medical practitioner to activate the spring 108 to retract the needle 100 by pressing down on the trigger button 134 in the direction indicated by the arrow labeled "B". By pressing on the trigger button 134 in the direction indicated by the arrow labeled "B", the medical practitioner can cause the trigger tab 132 to be slidably translated along the trigger tab slots 42. As the trigger tab 132 slidably translates along the trigger tab slots 42, the neck 112 becomes disengaged. With the neck 112 disengaged, the spring 108 is able to drive the needle carriage 106 along the elongate cavities 36, 12 to retract the needle 100.

Referring now to FIGS. 6A and 6B, cross-sectional views of some embodiments of the trigger portion 130 relative to the grip portion 30 are shown. FIG. 6A illustrates embodiments of the neck 112 engaged by the trigger tab 132 and FIG. 6B illustrates embodiments of the neck 112 disengaged from the trigger tab 132. In some cases, the keyhole opening 136 on the trigger tab 132 can comprise a narrow portion 137 and a larger portion 138. The narrow portion 137 can be sized and/or shaped to engage the neck 112. The larger portion 138 can be sized to permit the neck 112 to be disengaged from the keyhole opening 136 and/or to permit the carriage extension 122 to pass through the keyhole opening 136. As shown in FIG. 6A, with the trigger tab 132 in the engaged position, the neck 112 can be engaged by the narrow portion 137 of the keyhole opening 136 and the needle 100 maintained in the first position. As shown in FIG. 6B, as the medical practitioner presses down on the trigger button 134 in the direction indicated by the arrow labeled "B", the trigger tab 132 slides along the trigger tab slots 42, the neck 112 disengages with the narrower portion 137, and the larger portion 138 permits the carriage extension 122 to pass through the keyhole opening 136 thereby allowing the spring 108 to retract the needle 100. While FIGS. 6A and 6B illustrate a keyhole opening 136 mechanism to engage and disengage the neck 112, any other suitable mechanism as is known in the art can be used. For example, a pin or tab can be used to engage the neck 112 and the trigger button 134 can be configured to remove the pin or tab to disengage the neck 112.

In some embodiments, this application discloses methods of catheterization using catheter and needle assemblies comprising retracting needles. In some instances, these methods can include providing a catheter and needle assemblies as described above. The medical practitioner can begin by preparing a catheterization site on a patient. The medical practitioner can then remove the catheter and needle assembly 1 from any packaging. The medical practitioner can then grasp the assembly 1 by the gripping surfaces 38 and manipulate the assembly 1 so that the sharp distal point 104 of the elongate needle 100 is at a catheter insertion site. The medical practitioner can then insert the elongate needle 100 and the catheter 68 into the patient at a shallow angle at the catheter insertion site and access a blood vessel. In some cases, the medical practitioner can further advance the catheter 68 to achieve proper placement. The medical practitioner can confirm proper placement of the catheter by observing blood flashback into the open passageway 66 of the catheter and/or blood flashback along the tubing 72. The medical practitioner can then depress the trigger button 134 to activate the spring 108 to retract the elongate needle 100 into the second position. As the elongate needle 100 retracts into the grip portion 30 and hollow handle 10, the catheter hub 60 separates from the grip portion 30. The medical practitioner can then discard the grip portion 30 and hollow handle 10 that contain the sheathed elongate needle 100 with minimized risk of needle stick and/or contamination. When the elongate needle 100 retracts to the second position, the septum 78 seals the catheter hub 60 to prevent fluid escaping from the patient through the catheter 68. The medical practitioner can then infuse fluids to the patient through the side port forming the fluid junction 70 and/or through fluid connection 74. Alternately, the medical practitioner can then infuse fluids to the patient through the catheter 68 via the proximal fitting 76 of the catheter hub 60 using a connector that can traverse the septum 78.

Although the catheter and needle assembly 1 can be manufactured and assembled in any suitable manner, at least in some embodiments, the catheter and needle assembly 1 is assembled, cover 140 is positioned thereon, and the assembly 1 and cover 140 are placed within a sealed package. The sealed package can be formed from materials substantially resistant to contamination by infectious agents such as viruses and microbes. The sealed package can then be sterilized to render the infectious agents non-viable. Suitable sterilization conditions that render the infectious agents non-viable include chemical sterilants (e.g., ethylene oxide, hydrogen peroxide vapor, and other similar chemicals) and exposure to ionizing radiation (e.g., gamma rays, beta particles, and other similar types of radiation). Suitable materials for the sealed package include, but are not limited to, paper, waxed paper, plastic, thermoplastic film, non-woven materials, and other similar materials. After packaging and sterilization, the packaged assembly is considered sterile until the package is opened.

In some embodiments, when assembly 1 is manufactured, needle 100 is rotationally oriented in the assembly 1 so that a beveled surface of the sharp distal point 104 is substantially aligned with the trigger button 134. When the assembly 1 is unshielded in preparation for usage by the medical practitioner, the alignment of the beveled surface of the needle 100 and trigger button 134 substantially directs the medical practitioner's grasp of the hollow handle 10 to an intuitively proper position for insertion into the patient with the beveled surface facing upward. Following insertion of the needle 100 the medical practitioner is readily able to confirm the proper placement in the patient's blood vessel by observation of blood flashback in the open passageway 66 and/or within the tubing 72.

In some embodiments, when assembly 1 is manufactured, a lubricant can be applied to one or more parts of the assembly. For example, the lubricant can be applied to one or more of the needle 100, the catheter 68, the carriage extension 122, the needle carriage 106, and the spring 108. The lubricant can be applied to reduce friction between the components and/or to permit the lubricated components to slip more easily past each other. For example, lubricant can be applied to the needle carriage 106 and spring 108 to permit the needle carriage 106 to slide more easily from the first position to the second position. Likewise, lubricant can be applied to the needle 100 and or catheter 68 to ease entry of the needle into the patient's blood vessel and/or to ease removal of the needle 100 from the catheter 68. In some cases, the lubricant can comprise an antimicrobial agent such as chlorohexidine.

Although the catheter and needle assembly 1 can be manufactured from any suitable materials, at least in some embodiments, the hollow handle 10, the grip portion 30, the catheter hub 60, and the cover 140 are formed from thermoplastic polymeric resins such as polycarbonate, polystyrene, polypropylene, and other similar materials. The hollow handle 10 and the grip portion 30 can be formed from a substantially transparent material to allow the medical practitioner to visibly ascertain whether the needle 100 is in the first position or the second position. The catheter 68 can be formed from thermoplastic resins such as polytetrafluoroethylene (PTFE), polyurethane, and other similar materials. In some cases, the catheter 68 can be formed from thermoplastic hydrophilic polyurethane that softens with exposure to physiological conditions within the patient's body. The elongate needle 100, the spring 108, and the grommet 88 can be formed from a stainless steel alloy or other similar material.

The present disclosure discusses catheter and needle assemblies that can have many features. For example, some embodiments of the catheter and needle assemblies comprise a septum within the catheter hub. The septum is configured to seal when the needle is retracted, thereby sealing the catheter from an outside atmosphere to prevent fluid leakage. Also, in other embodiments, the catheter hub comprises a Y-port, tubing, and connectors. The Y-port can provide an access point for the medical practitioner to infuse fluids into the patient. Also, the tubing can provide the ability to observe blood flashback for a much longer time as a blood flow front progresses up the tubing. Another feature is a lower amount of drag when advancing the catheter. The lower amount of drag when advancing the catheter can be enabled by one or more of lubricating the needle and/or the catheter, the beveled surface of the sharp distal point of the needle, sizing and shaping the catheter and/or needle for reduced drag, and other similar features.

Yet another feature is the adaptability of the disclosed assemblies to other techniques known in the art. For example, the described assembly can be modified to place a catheter within a tortuous vessel anatomy by providing a flexible guidewire within the open bore of the needle. The assembly is inserted at the catheterization site as described above. Then the flexible guidewire is advanced into the blood vessel. The catheter is then further advanced into the blood vessel along the flexible guidewire. Then the flexible guidewire is retracted. The needle is then retracted as described above.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments, in all respects, are meant to be illustrative only and should not be construed to be limiting in any manner.

The invention claimed is:

1. A catheter system, comprising:
   a catheter assembly, comprising:
      a catheter hub, comprising a distal end, a proximal end, an open passageway extending through the distal end and the proximal end, and a side port;
      extension tubing in fluid communication with the side port;
      a catheter extending distally from the distal end; and
      a septum disposed within the open passageway; and
   a needle assembly, comprising:
      a hollow handle;
      a grip portion coupled to the hollow handle;
      a needle carriage configured to slidably translate within the hollow handle and the grip portion between a first position and a second position;
      a spring coupled to the needle carriage;
      an elongate needle comprising a sharp distal point, wherein the elongate needle is coupled to the needle carriage, wherein the sharp distal point of the elongate needle is disposed distal to the catheter when the needle carriage is in the first position, wherein the sharp distal point is disposed within the needle assembly when the needle carriage is in the second position; and
      a trigger portion comprising a trigger button and a keyhole opening, wherein the keyhole opening comprises a narrow portion and an enlarged portion compared to the narrow portion, wherein the narrow portion engages the needle carriage to maintain the elongate needle in the first position, wherein in response to pressing the trigger button, the needle carriage moves from the narrow portion of the keyhole opening to the enlarged portion of the keyhole opening and the spring retracts the needle carriage from the first position to the second position.

2. The assembly of claim 1, wherein the septum comprises a septum lumen disposed between a first septum opening and a second septum opening.

3. The assembly of claim 1, wherein the needle carriage comprises a carriage extension configured to detachably couple with a proximal fitting of the catheter hub.

4. The assembly of claim 1, wherein the needle carriage comprises a needle carriage cavity in fluid communication with an open bore of the elongate needle.

5. The assembly of claim 1, wherein the needle carriage comprises a neck configured to engage a trigger tab to maintain the elongate needle in the first position, wherein the neck comprises an indent, wherein the indent contacts the narrow portion.

* * * * *